(12) United States Patent
Hohlbein et al.

(10) Patent No.: US 7,735,174 B2
(45) Date of Patent: Jun. 15, 2010

(54) POWERED TOOTHBRUSH WITH MULTI-ACTION MOVEMENT

(75) Inventors: Douglas J. Hohlbein, Pennington, NJ (US); Al Sprosta, Union, NJ (US)

(73) Assignee: Colgate-Palmolive Company, New York, NY (US)

( * ) Notice: Subject to any disclaimer, the term of this patent is extended or adjusted under 35 U.S.C. 154(b) by 420 days.

(21) Appl. No.: 11/624,780

(22) Filed: Jan. 19, 2007

(65) Prior Publication Data

US 2008/0172811 A1    Jul. 24, 2008

(51) Int. Cl.
*A46B 13/00*    (2006.01)
*A47L 11/00*    (2006.01)

(52) U.S. Cl. .......................... 15/22.1; 15/22.2; 15/22.3
(58) Field of Classification Search ................... 15/22.1, 15/22.2, 22.3
See application file for complete search history.

(56) References Cited

U.S. PATENT DOCUMENTS

| 5,778,474 | A | * | 7/1998 | Shek | 15/22.1 |
| 5,842,245 | A | * | 12/1998 | Pai | 15/22.1 |
| 5,974,613 | A | | 11/1999 | Herzog | |
| 6,347,425 | B1 | | 2/2002 | Fattori et al. | |
| 6,760,946 | B2 | * | 7/2004 | DePuydt | 15/22.4 |
| 6,829,801 | B2 | | 12/2004 | Schutz | |
| 2003/0079305 | A1 | | 5/2003 | Takahata et al. | |
| 2003/0154568 | A1 | | 8/2003 | Boland et al. | |
| 2004/0016067 | A1 | | 1/2004 | Kraemer | |
| 2004/0168269 | A1 | | 9/2004 | Kunita et al. | |
| 2005/0011023 | A1 | | 1/2005 | Chan | |
| 2005/0039276 | A1 | * | 2/2005 | Kressner et al. | 15/22.1 |
| 2005/0102776 | A1 | | 5/2005 | Mathur | |
| 2005/0235439 | A1 | | 10/2005 | Braun et al. | |
| 2006/0010623 | A1 | | 1/2006 | Crossman et al. | |
| 2008/0010761 | A1 | * | 1/2008 | Blaustein et al. | 15/22.2 |

FOREIGN PATENT DOCUMENTS

| DE | 19701964 A1 | 7/1998 |
| EP | 1093770 A | 4/2001 |
| EP | 1700537 A | 9/2006 |
| WO | 03024353 A | 3/2003 |

OTHER PUBLICATIONS

International Search Report Dated Jul. 22, 2008.

* cited by examiner

*Primary Examiner*—Joseph J Hail, III
*Assistant Examiner*—Shantese McDonald
(74) *Attorney, Agent, or Firm*—Amy M. Fernandez

(57) ABSTRACT

A powered toothbrush includes a handle having a neck. A head is mounted to the neck and has a first portion and a second portion. A plurality of tuft blocks is mounted to the second portion, with each tuft block having a tooth cleaning element. At least one projection is positioned on one of the first and second portions, each projection engaging one of the tuft blocks and pivoting the tuft block with respect to the second portion. A drive assembly is operably connected to one of the first and second portions to drive the one of the first and second portions in an oscillating manner.

11 Claims, 5 Drawing Sheets

POWERED TOOTHBRUSH WITH MULTI-ACTION MOVEMENT

FIELD OF THE INVENTION

This invention relates generally to a toothbrush, and, in particular, to a powered toothbrush having a plurality of moving tuft elements.

BACKGROUND OF THE INVENTION

A variety of toothbrush configurations exist that have stationary and/or mechanically-driven movable cleaning elements. These conventional toothbrushes are dedicated to tooth cleaning/polishing operations and typically include a head portion directed to the cleaning/polishing operation, and a handle portion. The head typically has a flat or slightly altered surface to which the cleaning elements are attached, or to which mechanically-driven movable carriers for the cleaning elements are attached.

Many powered toothbrushes have a round head with cleaning elements that move in an oscillating fashion with respect to the brush head. Such brushes may have a round tuft block that oscillates through a range of about 10 to about 30 degrees. The cleaning elements are typically rigidly mounted to the moving tuft block and, therefore, all go through the same angular range of movement.

It would be desirable to provide a toothbrush that reduces or overcomes some or all of the difficulties inherent in prior known devices. Particular objects and advantages will be apparent to those skilled in the art, that is, those who are knowledgeable or experienced in this field of technology, in view of the following disclosure of the invention and detailed description of certain embodiments.

SUMMARY

The principles of the invention may be used to advantage to provide a powered toothbrush having a plurality of moving tuft elements. In accordance with a first aspect, a powered toothbrush includes a handle having a neck. A head is mounted to the neck and has a first portion and a second portion. A plurality of tuft blocks is mounted to the second portion, with each tuft block having a tooth cleaning element. At least one projection is positioned on one of the first and second portions, each projection engaging one of the tuft blocks and pivoting the tuft block with respect to the second portion. A drive assembly is operably connected to one of the first and second portions to drive the one of the first and second portions in an oscillating manner In accordance with another aspect, a powered toothbrush includes a handle having a neck. A head is mounted to the neck and has a first portion having a plurality of slots formed in an upper surface thereof and a second portion abutting the upper surface of the first portion. A plurality of tuft blocks is pivotally mounted to the second portion, with each tuft block having a guide pin extending from a lower surface thereof, and each guide pin being received in a corresponding slot in the first portion. A slot is formed in one of the first portion and the second portion. A drive assembly has a rotatable shaft with a remote-most end having an offset portion received in the slot to move the one of the first portion and the second portion in an oscillating manner.

In accordance with a further aspect, a powered toothbrush includes a handle having a neck. A head is mounted to the neck and has a base portion having a plurality of curved slots formed in an upper surface thereof and a second portion abutting the upper surface of the fixed portion, with the second portion including a plurality of notches about its peripheral edge, and an aperture extending through the second portion from each notch to a lower surface of the second portion. Each of a plurality of tuft blocks is pivotally mounted in a notch in the second portion, with each tuft block having a guide pin extending from a lower surface thereof and each guide pin extends through an aperture in the second portion and is received in a corresponding slot in the base portion. A drive assembly includes a power source, and a motor having a shaft with an offset portion, with the offset portion engaging the second portion to move the second portion in an oscillating manner such that the tuft blocks pivot in a radially extending plane with respect to the second portion.

These and additional features and advantages disclosed here will be further understood from the following detailed disclosure of certain embodiments.

Figure 1:
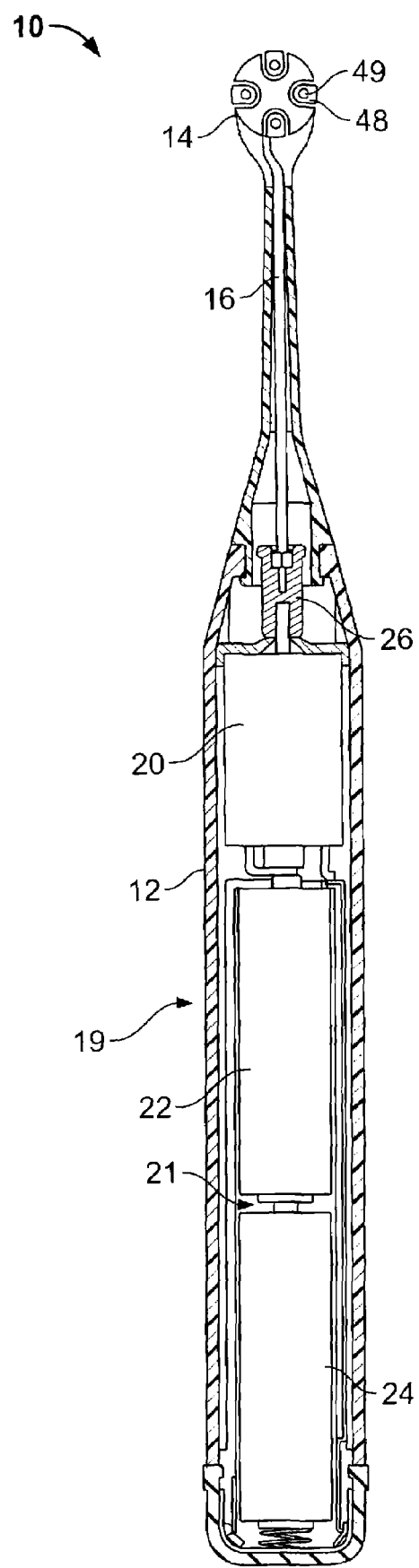
FIG. 1 is a sectional bottom view of a toothbrush.

The figures referred to above are not drawn necessarily to scale and should be understood to provide a representation of the invention, illustrative of the principles involved. Some features of the toothbrush depicted in the drawings have been enlarged or distorted relative to others to facilitate explanation and understanding. The same reference numbers are used in the drawings for similar or identical components and features shown in various alternative embodiments. Toothbrushes as disclosed herein would have configurations and components determined, in part, by the intended application and environment in which they are used.

DETAILED DESCRIPTION OF CERTAIN PREFERRED EMBODIMENTS

Referring to the drawings, in FIG. 1 a toothbrush 10 includes a handle 12 at a first end of the toothbrush, a head 14 at a second end of the toothbrush, and a rotatable shaft 16 extending from handle 19 to head 4. Handle 12 provides compartments for holding a drive assembly 19 including an electric motor 20 and a power source 21. In certain embodiments, power source 21 is formed of two batteries 22, and 24. A shaft coupling 26 is arranged to grip one end of shaft 16 and allow the shaft to be pulled out for cleaning or replacement.

Figure 2:
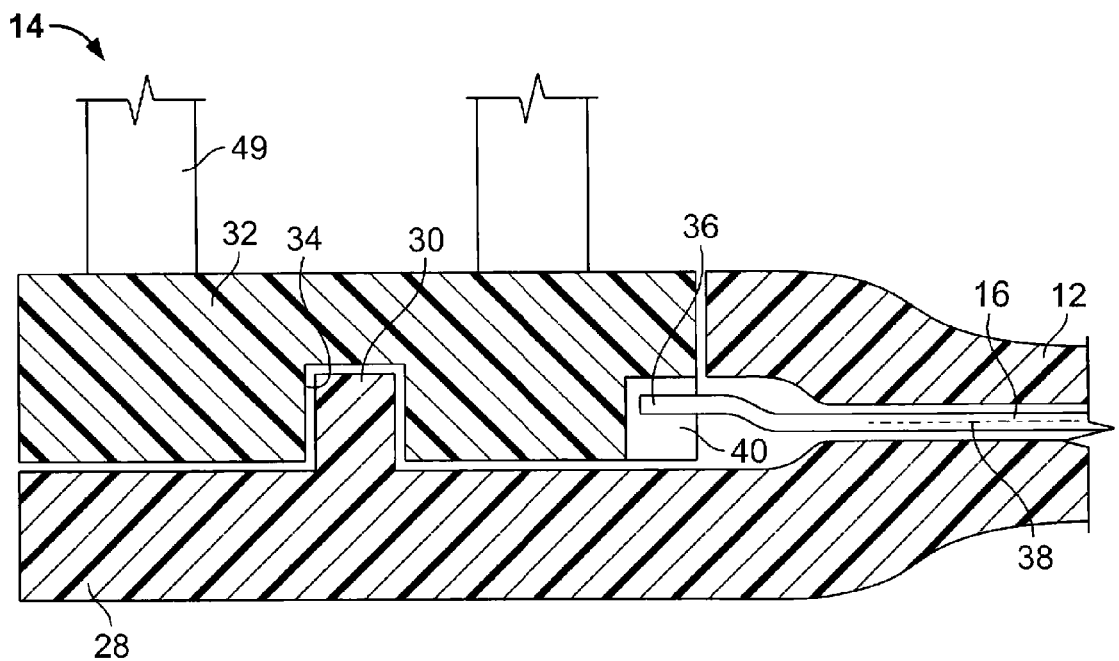
FIG. 2 is a sectional view side view of the head of the toothbrush of FIG. 1.
Figure 3:
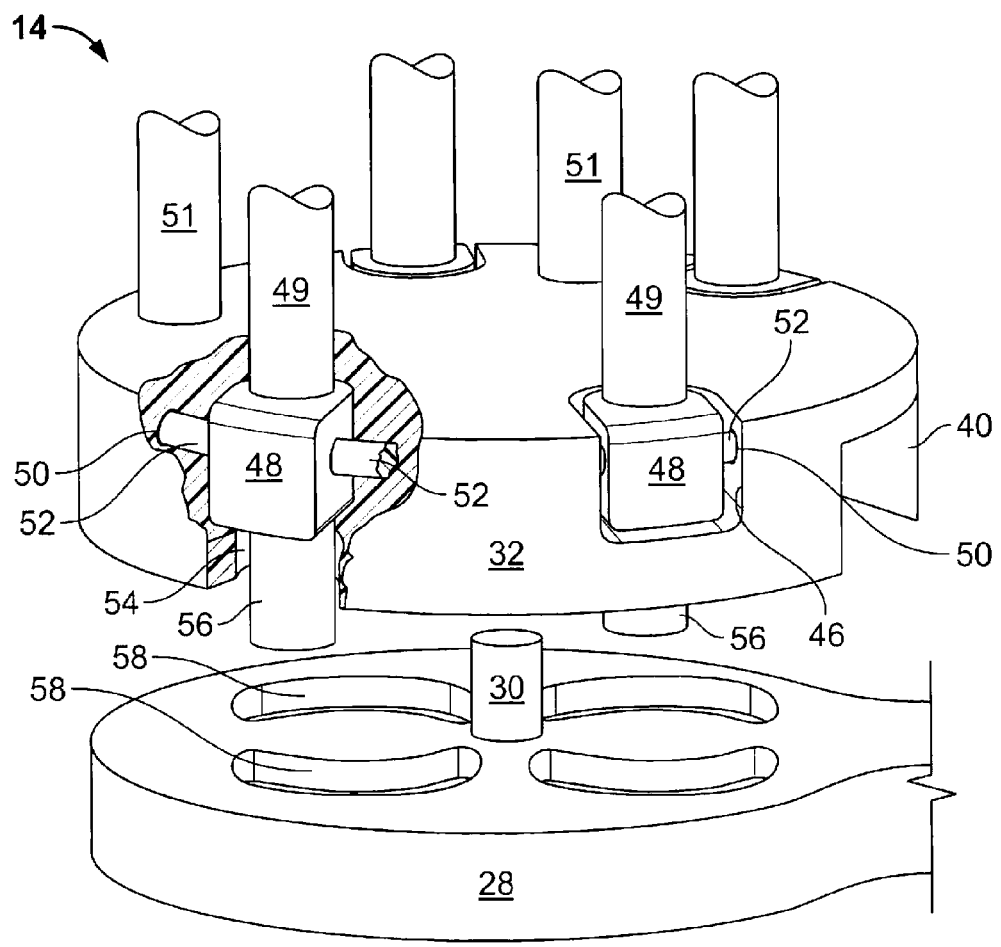
FIG. 3 is a perspective exploded view of a portion of the head of the toothbrush of FIG. 1.

In certain embodiments, as seen in FIGS. 2-3, head 14 is formed of a first portion 28 having an axially extending post 30, and a second portion 32 having a central recess 34 that receives post 30 such that post 30 provides a rotational pivot axis for second portion 32 of head 14. Shaft 16 has a remote-most end 36 that is off-set from a central longitudinal axis 38 of shaft 16.

Remote-most end 36 fits into a slot 40 formed in second portion 32 of head 14. When shaft 16 is rotated by motor 20, remote-most end 36 describes a circle about shaft 16 and drivingly engages slot 40 to cause second portion 32 of head 14 to move in an oscillating fashion. Thus, second portion 32 oscillates forwards and backwards about post 30. The width of slot 40 is preferably generally the same as the diameter of end 36 to leave minimum play; thus keeping noise to a minimum during use. Shaft 16 is preferably of unitary, that is, one-piece construction, and is formed of a single length of a thin rod and shaped as shown. However, it is possible to arrange for remote-most end 36 to be separately formed or provided and fixed to a straight end part of shaft 16.

As seen in FIG. 3, second portion 32 has a plurality of notches 46. A tuft block 48 is pivotally received in each notch 46. Tuft blocks 48 have tooth cleaning elements 49 extending upwardly from an upper surface thereof. As use herein, the term "tooth cleaning elements" includes any type of structure that is commonly used or is suitable for use in providing oral health benefits (e.g., tooth cleaning, tooth polishing, tooth whitening, massaging, stimulating, etc.) by making intimate contact with portions of the teeth and gums. Such tooth cleaning elements include but are not limited to tufts of bristles that can be formed to have a number of different shapes and sizes and elastomeric cleaning members that can be formed to have a number of different shapes and sizes, or a combination of both tufts of bristles and elastomeric cleaning members.

Tuft blocks 48 may be formed with bristles of the same or different bristle materials (such as nylon bristles, spiral bristles, rubber bristles, etc.). Moreover, while tooth cleaning elements 49 may be arranged so that they are generally perpendicular to the upper surface of tuft block 48, some or all of tooth cleaning elements 49 may be angled at various angles with respect to the upper surface of tuft block 48.

Tooth cleaning elements 49 may be arranged by any conventional method. For example, the tooth cleaning elements 49 may be stapled to tuft block 48. In certain embodiments, tooth cleaning elements 49 in the form of strands or bristles can be attached via in-molded technology (IMT) methods that generally require small cross-sections of material into which the strands are permanently attached. The strands utilizing IMT methods may be attached during formation of handle 12 or during formation of head 14, which is the portion of toothbrush 10 to which the strands and other materials are attached.

In other embodiments, tooth cleaning elements 49 in the form of strands or bristles may be attached via anchor free tufting (AFT). In the AFT brush making process, described in detail in U.S. Pat. No. 6,779,851, nylon is fed into a pre-molded plate that can be made from any thermoplastic or elastomer material or combination thereof. This nylon may be processed into bristle tufts of various sizes and shapes. The non-use or proximal end of the nylon is heated and melted to retain the nylon in the brush head when a reasonable pulling force is applied. This head plate may then be ultrasonically welded to a pre-molded handle that has a peripheral wall or frame on which the head plate will rest and become fused to the handle.

In certain embodiments, second portion 32 includes one or more fixed tooth cleaning elements 51 directly secured to second portion 32. Although two such fixed tooth cleaning elements 51 are shown in FIG. 3, it is to be appreciated that any number of fixed tooth cleaning elements 51 can be located on second portion 32.

Each notch 46 has a pair of opposed pivot recesses 50. Each tuft block 48 has a pair of opposed pivot pins 52, each of which is pivotally received in a corresponding pivot recess 50. The engagement of pivot pins 52 with pivot recesses 50 allow each tuft block 48 to pivot in a radially extending plane with respect to second portion 32.

It is to be appreciated that each pair of pivot pins 52 associated with a tuft block 48 may be separate elements secured to tuft block 48. In certain embodiments, however, pivot pins 32 may be opposite ends of a single unitary pivot pin extending through tuft block 48.

An aperture 54 extends from a lower surface of each notch 46 to the lower surface of second portion 32. A projection, in the form of a guide pin 56 in the illustrated embodiment, extends downwardly from a lower surface of each tuft block 48, extending through a corresponding aperture 54 such that the ends of guide pins 36 extend beyond the lower surface of second portion 32.

Figure 4:
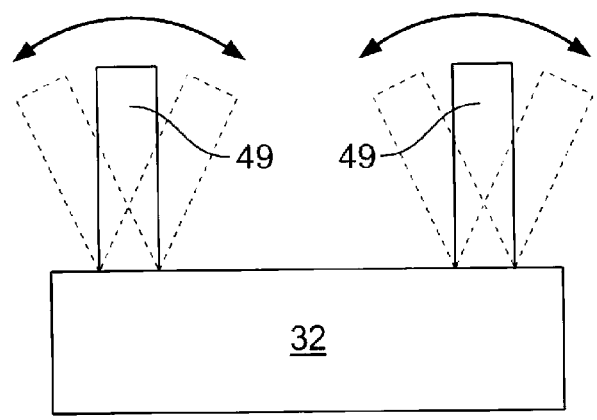
FIG. 4 is an elevation view of a second portion of the head of toothbrush of FIG. 1, showing relative movement of tuft elements of the toothbrush.

A plurality of slots 58 is formed in an upper surface of first portion 28, with each guide pin 56 being slidingly received in a corresponding slot 58, such that slots 58 act as guide tracks for guide pins 56. In certain embodiments, slots 58 are arcuate, and curve inwardly toward an interior of first portion 28. Thus, as second portion 32 oscillates, guide pins 56 are driven back and forth along corresponding slots 58. As guide pins 56 are driven along slots 58, tuft blocks 48 pivot about pivot pins 52, causing tooth cleaning elements 49 to pivot in the direction of arrow A along, a radially extending plane with respect to second portion 32, as seen in FIG. 4.

As illustrated in FIG. 3, second portion 32 is shown with four tuft blocks 48. It is to be appreciated that any number of tuft blocks 48 may be incorporated in second portion 32. Additionally, as noted above, tooth cleaning elements 49 of each tuft block 48 may be bristles, elastomeric elements or any other tooth cleaning element.

First portion 28 and second portion 32 are shown here having a substantially cylindrical shape. It is to be appreciated that first and second portion 28, 32 may have any desired shape.

Figure 5:
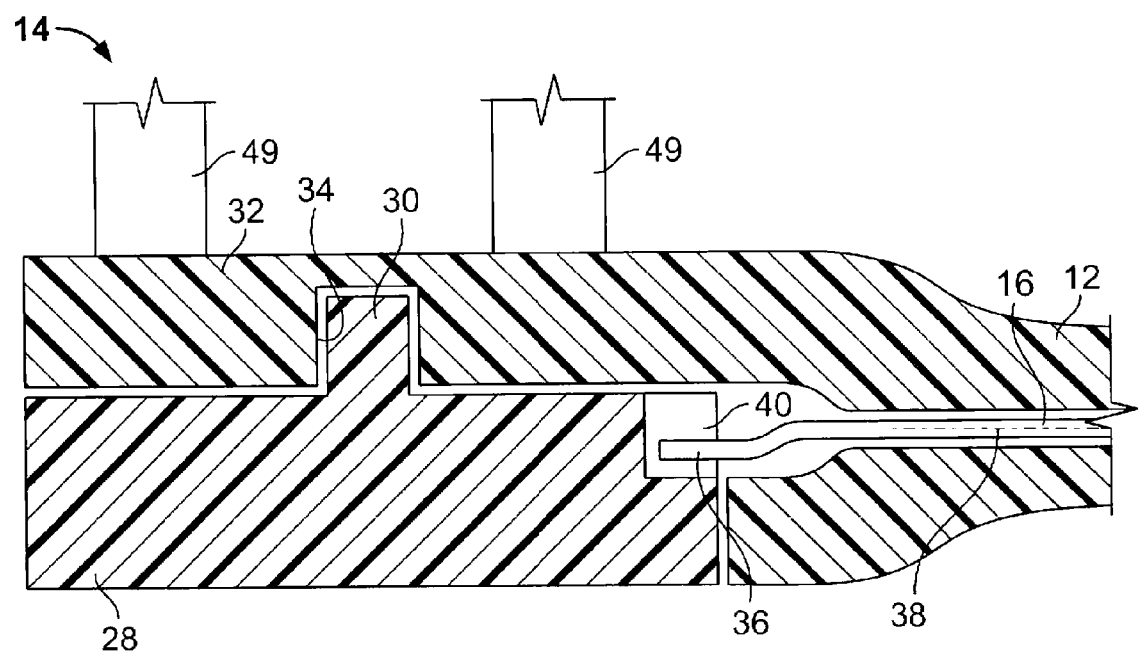
FIG. 5 is a section view of an alternative embodiment of the head of the toothbrush of FIG. 1.

In certain other embodiments, as seen in FIG. 5, slot 40 can be formed in first portion 28 such that first portion 48 moves while second portion 32 remains fixed with respect to handle 12. In such an embodiment, first portion 28 is driven by remote-most end 36 of shaft 16 in an oscillating manner. Guide pins 56 will move along slots 58 in the same manner as discussed above with respect to FIGS. 2-3.

Figure 6:
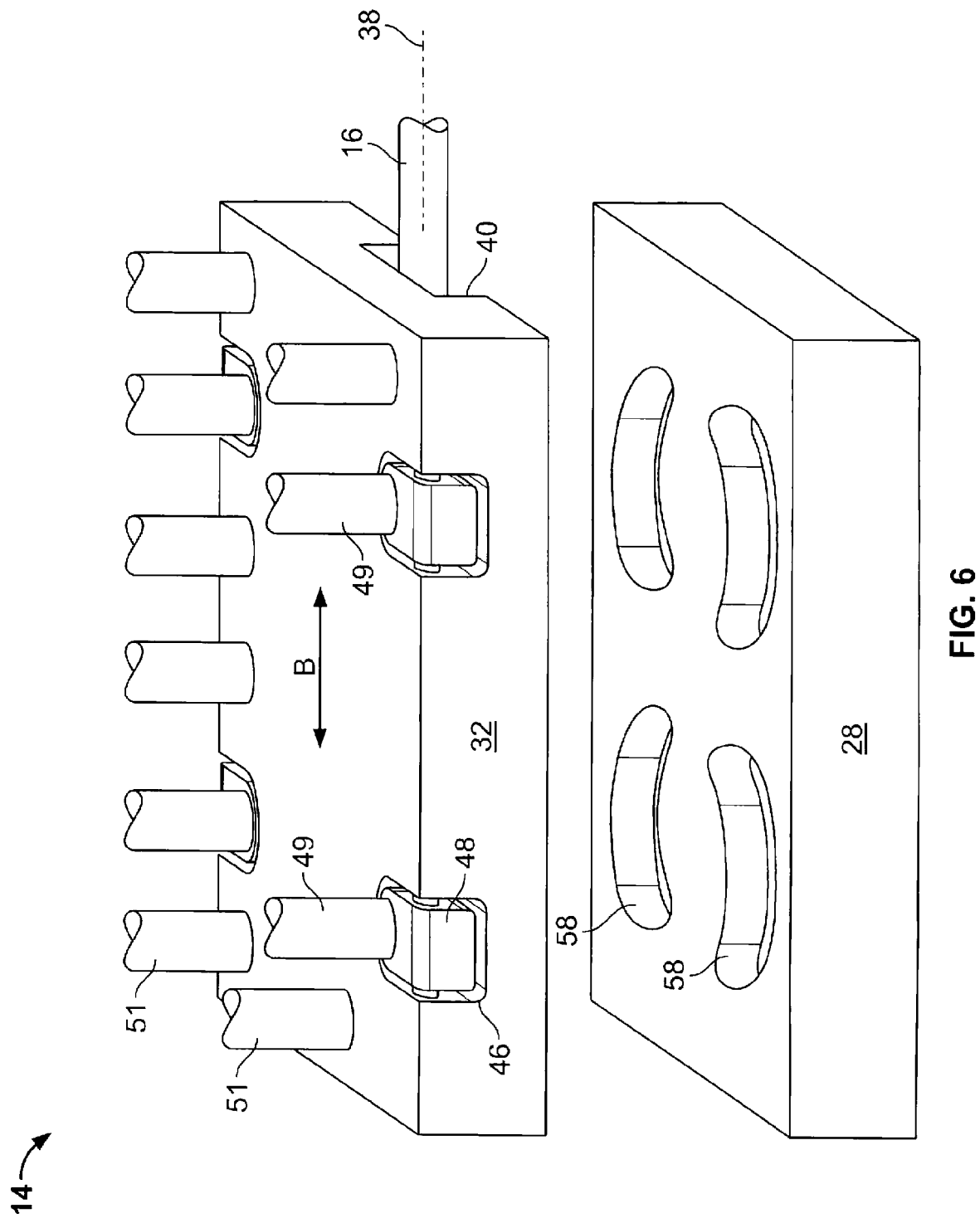
FIG. 6 is a perspective exploded view of an alternative embodiment of the head of FIG. 1.

In certain embodiments, as shown in FIG. 6, toothbrush 10 is configured such that shaft 16 drives second portion 32 in linear fashion, in the direction of arrow B, substantially parallel to longitudinal axis 38 of shaft 16. It is to be appreciated that, as discussed above, slot 40 may be formed in first portion 28 such that shaft 16 engages first portion 28 and oscillates first portion 28 with respect to second portion 32. As illustrated here, first and second portion 28, 32 have substantially rectangular shapes. However, it is to be appreciated that first and second portions 28, 32 may have other shapes as well.

Figure 7:
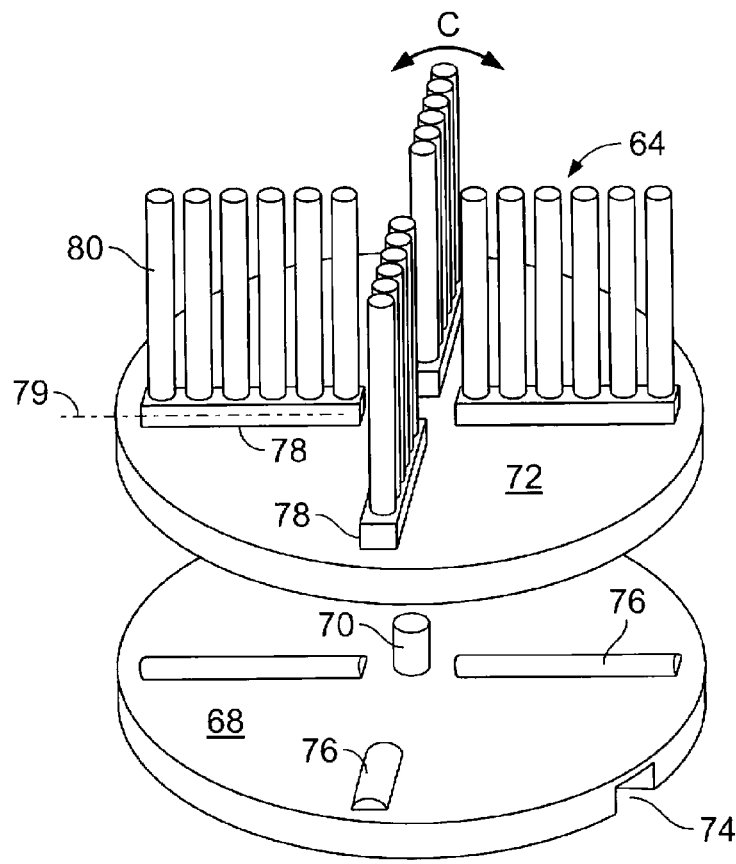
FIG. 7 is a perspective exploded view of another alternative embodiment of the head of FIG. 1.

Another embodiment is shown in FIG. 7, in which a head 64 includes a first portion 68 having an axially extending post 70, and a second portion 72 having a central recess (not visible) that receives post 70 such that post 70 provides a rotational pivot axis for second portion 72 of head 64. A slot 74 formed in first portion 68 receives remote-most end 36 of shaft 16 such that first portion 68 rotates in oscillating fashion as shaft 16 rotates.

First portion 68 includes a plurality of projections on its upper surface, which are in the form of semi-cylindrical projections 76, with a longitudinal axis of each semi-cylindrical projection 76 extending along a radius of first portion 68.

Second portion 72 is formed of a flexible material. In the illustrated embodiment second portion 72 is a flexible membrane. Second portion may be formed of any suitable flexible or moldable material such as a thermoplastic elastomer (TPE), thermoplastic urethane (TPU), rubber or silicone, for example.

Each of a plurality of tuft blocks 78 having a plurality of tooth cleaning elements 80 is secured to the exposed upper surface of second portion 72. Each tuft block 78 has a longitudinal axis 79 that extends along a radius of second portion 72. Tuft blocks 78 may be adhesively secured to second portion 72, or secured in any other suitable manner. As first portion 68 is driven in oscillating fashion as shaft 16 rotates, projections 76 displace flexible second portion 72 upwardly thereby causing tuft blocks 78 to move up and down, as if riding a wave. As tuft blocks 78 move, tooth cleaning elements 80 are caused to pivot back and forth in the direction of arrow C along a plane extending substantially perpendicular to a radius of second portion 72 and the exposed upper surface of second portion 72.

It is to be appreciated that the height of the upward movement of tuft blocks 72, the degree to which tooth cleaning elements 80 are rotated, as well as the duration and frequency with which projections 76 engage tuft blocks 72 through second portion 72 can be controlled by altering the size, shape and location of projections 76.

Figure 8:
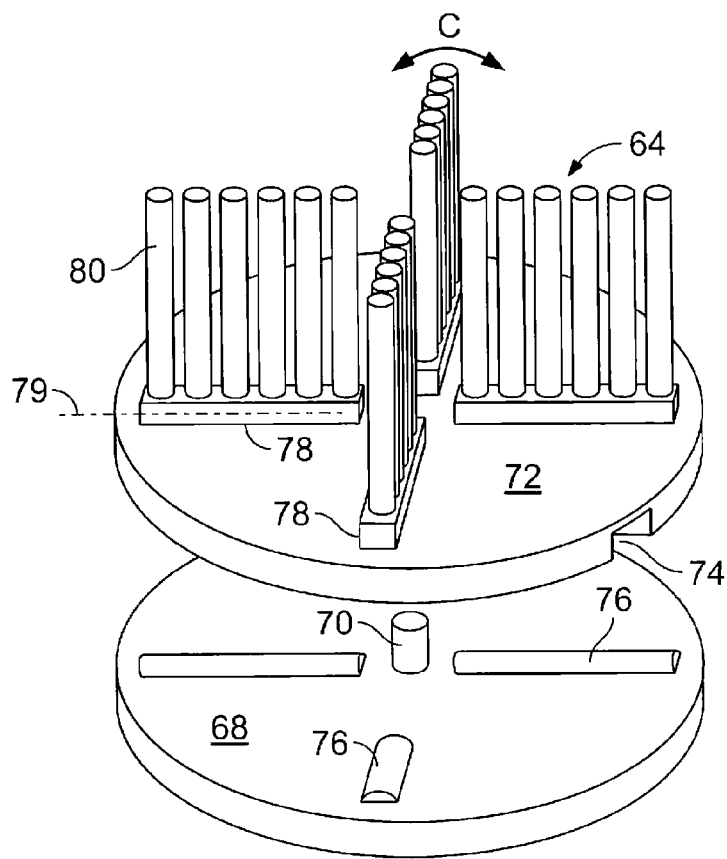
FIG. 8 is a perspective exploded view of yet another alternative embodiment of the head of FIG. 1.

In other embodiments, as seen in FIG. 8, slot 74 can be formed in second portion 72 to receive remote-most end 36 of shaft 16 such that second portion 72 is driven while first portion 68 remains fixed with respect to handle 12.

Although first and second portions 68, 72 are shown here having a substantially circular shape, it is to be appreciated that first and second portions 68, 72 may have other shapes as well.

In light of the foregoing disclosure of the invention and description of various embodiments, those skilled in this area of technology will readily understand that various modifications and adaptations can be made without departing from the scope and spirit of the invention. All such modifications and adaptations are intended to be covered by the following claims.

The invention claimed is:

1. A powered toothbrush comprising:
a handle having a neck;
a head mounted to the neck and having a first portion and a second portion;
a plurality of tuft blocks mounted to the second portion, each tuft block having a tooth cleaning element;
at least one projection on one of the first and second portions, the projection engaging one of the tuft blocks and pivoting the tuft block with respect to the second portion;
a drive assembly operably connected to one of the first and second portions to drive the one of the first and second portions in an oscillating manner;
a plurality of slots formed in an upper surface of the first portion; and
wherein the tuft blocks are pivotally mounted to the second portion, each tuft block having a guide pin extending from a lower surface thereof, each guide pin being received in a corresponding slot in the first portion.

2. The powered toothbrush of claim 1, wherein the first and second portion are substantially cylindrical and the tuft blocks pivot in a radially extending plane with respect to the second portion.

3. The powered toothbrush of claim 1, wherein each slot is curved.

4. The powered toothbrush of claim 3, wherein each slot curves inwardly toward an interior of the first portion.

5. The powered toothbrush of claim 1, wherein the second portion includes a plurality of notches, each notch having a pair of opposed pivot recesses, a tuft block being received in each notch; and
wherein each tuft block includes a pair of opposed pivot pins, each pivot pin being received in a pivot recess.

6. The powered toothbrush of claim 5, wherein the pivot pins extend substantially perpendicular to a radius of the second portion.

7. A powered toothbrush comprising:
a handle having a neck;
a head mounted to the neck and having a first portion having a plurality of slots formed in an upper surface thereof and a second portion abutting the upper surface of the first portion;
a plurality of tuft blocks pivotally mounted to the second portion, each tuft block having a guide pin extending from a lower surface thereof, each guide pin being received in a corresponding slot in the first portion;
a slot formed in one of the first portion and the second portion;
a drive assembly having a rotatable shaft with a remote-most end having an offset portion received in the slot to move the one of the first portion and the second portion in an oscillating mariner.

8. A powered toothbrush comprising:
a handle having a neck;
a head mounted to the neck and having a base portion having a plurality of curved slots formed in an upper surface thereof and a second portion abutting the upper surface of the fixed portion, the second portion including a plurality of notches about its peripheral edge, an aperture extending through the second portion from each notch to a lower surface of the second portion;
a plurality of tuft blocks, each tuft block pivotally mounted in a notch in the second portion, each tuft block having a guide pill extending from a lower surface thereof, each guide pin extending through an aperture in the second portion and being received in a corresponding slot in the base portion; and
a drive assembly comprising a power source, and a motor having a shaft with an offset portion, the offset portion engaging the second portion to move the second portion in an oscillating mariner such that the tuft blocks pivot in a radially extending plane with respect to the second portion.

9. A powered toothbrush comprising:
a handle having a neck;
a head mounted to the neck and having a first portion and a second portion;
a plurality of tuft blocks mounted to the second portion, each tuft block having a tooth cleaning element;
at least one projection on one of the first and second portions, the projection engaging one of the tuft blocks and pivoting the tuft block with respect to the second portion;
a drive assembly operably connected to one of the first and second portions to drive the one of the first and second portions in an oscillating manner;
wherein the second portion is a flexible membrane; and
wherein a plurality of projections are formed on an upper surface of the first portion, the projections engaging the second portion and causing the tuft blocks to pivot.

10. The powered toothbrush of claim 9, wherein the projections are semi-cylindrically shaped.

11. The powered toothbrush of claim 10, wherein the first portion is substantially cylindrical, and a longitudinal axis of each semi-cylindrically shaped projection extends substantially parallel to a radius of the first portion.

* * * * *